United States Patent
Kaiser et al.

(10) Patent No.: US 6,930,493 B2
(45) Date of Patent: Aug. 16, 2005

(54) METHOD AND APPARATUS FOR MONITORING DETERGENT CONCENTRATION IN A DECONTAMINATION PROCESS

(75) Inventors: Herbert J. Kaiser, Pontoon Beach, IL (US); David G. Allen, Willoughby, OH (US); Michael A. Centanni, Parma, OH (US); Mark D. McGinley, Concord, OH (US)

(73) Assignee: STERIS Inc., Temecula, CA (US)

( * ) Notice: Subject to any disclaimer, the term of this patent is extended or adjusted under 35 U.S.C. 154(b) by 0 days.

(21) Appl. No.: 10/931,186

(22) Filed: Aug. 31, 2004

(65) Prior Publication Data

US 2005/0017728 A1 Jan. 27, 2005

Related U.S. Application Data

(63) Continuation-in-part of application No. 10/389,036, filed on Mar. 14, 2003.

(51) Int. Cl.⁷ ............................................. G01R 27/26
(52) U.S. Cl. ..................................................... 324/663
(58) Field of Search ......................... 324/664, 658–666; 422/28–31, 82.01, 82.02, 83, 96; 210/754, 96.1

(56) References Cited

U.S. PATENT DOCUMENTS 3,636,444 A   1/1972 Strawn et al. ................ 324/61
3,778,706 A   12/1973 Thompson ................... 324/61
3,816,811 A   6/1974 Cmelik ...................... 324/61 R (Continued)

OTHER PUBLICATIONS

U.S. Appl. No. 10/456,378, filed Jun. 6, 2003, Centanni, entitled: Method and Apparatus for Formulating and Controlling Chemical Concentrations in a Solution.
U.S. Appl. No. 10/456,380, filed Jun. 6, 2003, Centanni, entitled: Method and Apparatus for Formulating and Controlling Chemical Concentrations in a Gas Mixture.
U.S. Appl. No. 10/872,227, filed Jun. 18, 2004, Kaiser et al., entitled: Method and Apparatus for Monitoring the Purity and/or Quality of Steam.
U.S. Appl. No. 10/896,609, filed Jul. 21, 2004, Kaiser et al., entitled: Method and Apparatus for Real Time Monitoring of Metalli Cation Concentrations in a Solution.
U.S. Appl. No. 10/900,745, filed Jul. 28, 2004, Kaiser et al., entitled: Method and Apparatus for Monitoring the State of a Chemical Solution for Decontamination of Chemical and Biological Warfare Agents.

(Continued)

*Primary Examiner*—Anjan Deb
*Assistant Examiner*—Amy He
(74) *Attorney, Agent, or Firm*—Kusner & Jaffe; Michael A. Centanni (57) ABSTRACT

A method and apparatus for monitoring the concentration of a detergent in a detergent solution. A capacitive sensor is exposed to the detergent solution, and electrical properties of the capacitive sensor are responsive to changes in the concentration of detergent in the detergent solution.

17 Claims, 5 Drawing Sheets

U.S. PATENT DOCUMENTS

| | | | |
|---|---|---|---|
| 4,031,742 A | * 6/1977 | Michael et al. | 73/40.7 |
| 4,158,810 A | 6/1979 | Leskovar | 324/127 |
| 4,219,776 A | 8/1980 | Arulanandan | 324/323 |
| 4,427,772 A | 1/1984 | Kodera et al. | 435/27 |
| 4,509,522 A | 4/1985 | Manuccia et al. | 128/634 |
| 4,525,265 A | 6/1985 | Abe et al. | 204/403 |
| 4,674,879 A | 6/1987 | Gregorig et al. | 356/301 |
| 4,769,593 A | 9/1988 | Reed et al. | 324/668 |
| 4,849,687 A | 7/1989 | Sims et al. | 324/668 |
| 4,857,152 A | 8/1989 | Armstrong et al. | 204/1 T |
| 5,151,660 A | 9/1992 | Powers et al. | 324/689 |
| 5,157,968 A | 10/1992 | Zfira | 73/149 |
| 5,171,523 A | * 12/1992 | Williams | 422/20 |
| 5,179,926 A | 1/1993 | Ament | 123/494 |
| 5,243,858 A | 9/1993 | Erskine et al. | 73/204.26 |
| 5,364,510 A | 11/1994 | Carpio | 204/153.1 |
| 5,439,569 A | 8/1995 | Carpio | 204/153.1 |
| 5,459,568 A | 10/1995 | Yano et al. | 356/336 |
| 5,470,754 A | 11/1995 | Rounbehler et al. | 436/106 |
| 5,600,142 A | 2/1997 | Van Den Berg et al. | 250/339.13 |
| 5,847,276 A | 12/1998 | Mimken et al. | 73/453 |
| 5,882,590 A | 3/1999 | Stewart et al. | 422/28 |
| 5,997,685 A | 12/1999 | Radhamohan et al. | 156/345 |
| 6,162,409 A | 12/2000 | Skelley et al. | 423/239.1 |
| 6,369,387 B1 | 4/2002 | Eckles | 250/343 |
| 6,454,874 B1 | 9/2002 | Jacobs et al. | 134/18 |
| 6,614,242 B2 | 9/2003 | Matter et al. | 324/698 |
| 6,660,231 B2 | 12/2003 | Moseley | 422/98 |
| 6,706,648 B2 | 3/2004 | Yamazaki et al. | 438/790 |
| 2002/0014410 A1 | 2/2002 | Silveri et al. | 204/412 |
| 2002/0033186 A1 | 3/2002 | Verhaverbeke et al. | 134/26 |
| 2002/0076492 A1 | 6/2002 | Loan et al. | 427/255.28 |
| 2002/0109511 A1 | * 8/2002 | Frank | 324/663 |
| 2002/0111040 A1 | 8/2002 | Yamazaki et al. | 438/783 |
| 2002/0157686 A1 | 10/2002 | Kenny et al. | 134/1.3 |
| 2003/0063997 A1 | 4/2003 | Fryer et al. | 422/3 |
| 2003/0102007 A1 | 6/2003 | Kaiser | 134/1 |
| 2003/0157587 A1 | 8/2003 | Gomez et al. | 435/30 |
| 2004/0029257 A1 | 2/2004 | Dutil et al. | 435/266 |
| 2004/0079395 A1 | 4/2004 | Kim et al. | 134/30 |
| 2004/0178799 A1 | 9/2004 | Korenev et al. | 324/453 |
| 2004/0178802 A1 | 9/2004 | Centanni | 324/662 |
| 2004/0178803 A1 | 9/2004 | Centanni | 324/662 |
| 2004/0178804 A1 | 9/2004 | Allen et al. | 324/662 |
| 2004/0262170 A1 | 12/2004 | Centanni | 205/782 |

OTHER PUBLICATIONS

T. J. Buckley et al., "Toroidal Cross Capacitor for Measuring the Dielectric Constant of Gases," Review of Scientific Instruments, vol. 71, No. 7, Jul. 2000, pp. 2914–2921.

Gross et al., "The Dielectric Constants of Water Hydrogen Peroxide and Hydrogen Peroxide–Water Mixtures," L. Amer. Chem. Soc., vol. 72, 1950, pp. 2075–2080, May 1950.

"Humidty Sensor Theory and Behavior," Psychometrics and Moisture, Honeywell HVAC, Nov. 27, 2002.

Philipp, "Charge Transfer Sensing," 1997, no month available.

Wojslaw, "Everything You Wanted to Know About Digitally Programmable Potentiometers," Catalyst Semiconductor, Inc., Oct. 17, 2001, Publication No. 6009.

Kittel, "Introduction to Solid State Physics," Fourth Edition, John Wiley & Sons, Inc., 1971, no month available.

Philipp, "The Charge Transfer Sensor," Sensors Magazine, Oct. 1999.

* cited by examiner

METHOD AND APPARATUS FOR MONITORING DETERGENT CONCENTRATION IN A DECONTAMINATION PROCESS

RELATED APPLICATIONS

This application is a continuation-in-part of U.S. patent application Ser. No. 10/389,036, filed Mar. 14, 2003, entitled "Method and Apparatus for Measuring Chemical Concentration in a Fluid," and is hereby fully incorporated herein by reference.

FIELD OF THE INVENTION

The present invention relates generally to decontamination systems, and more particularly to a method and apparatus for monitoring the concentration of a detergent used in a decontamination process.

BACKGROUND OF THE INVENTION

As used herein, the term "decontamination" refers to processes, including, but not limited to, "deactivation of biocontamination," "deactivation of chemical contamination," "sterilization," "disinfection" and "sanitization."

Detergents are widely used in a variety of decontamination processes, including, but not limited, to healthcare decontamination processes, pharmaceutical manufacturing processes, as well as household/domestic washing (such as clothes washing and dish washing). The detergents are typically comprised of one or more active detergent chemical components that are combined with water to form a detergent solution. As used herein, the term "detergent" refers to the one or more detergent chemical components.

Detergent used in healthcare decontamination processes includes, but is not limited to, enzymatic, alkaline, acidic and neutral detergent (e.g., liquid detergents, such as Renu-Klenz, Liqui-Jet 2, Klenzyme, Enzycare 2, NpH-Klenz, Instru-Klenz, and Criti-Klenz, sold by STERIS Corporation). Detergent used in pharmaceutical manufacturing processes includes, but is not limited to, alkaline, acidic, oxidative (e.g., bleach) and neutral detergent (e.g., liquid detergents such as CIP 100, CIP 200, CIP 220, CIP 300, CIP 150, sold by STERIS Corporation). The detergent may be primarily inorganic-based or organic-based.

The active ingredients for some of the abovementioned detergents are identified in the table set forth below:

| Detergent | Active Ingredients |
| --- | --- |
| Renu-Klenz | Blend of nonioinic surfactants |
|  | Neutral pH |
| Liqui-Jet 2 | Anionic Surfactant |
|  | Ethylenediaminetetraacetic acid |
|  | Potassium and Sodium Hydroxide |
|  | Silicates |
| Klenzyme | Protease Enzyme |
|  | Anionic Surfactant |
|  | Buffers |
| Enzycare 2 | Protease Enzymes |
|  | Anionic Surfactant |
|  | Buffers |
| NpH-Klenz | Blend of nonionic surfactants |
|  | Neutral pH |
| Instru-Klenz | Ethylenediaminetetraacetic acid |
|  | Amphoteric Surfactant |

-continued

| Detergent | Active Ingredients |
| --- | --- |
| Criti-Klenz | Ethylenediaminetetraacetic acid |
|  | Amphoteric Surfactant |
| CIP 100 | Potassium Hydroxide |
|  | Amphoteric Surfactant |
|  | Ethylenediaminetetraacetic acid |
| CIP 200 | Phosphoric Acid |
|  | Amphoteric Surfactant |
| CIP 220 | Glycolic Acid |
|  | Amphoteric Surfactant |
| CIP 300 | Amphoteric Surfactant |
|  | Nonioinic Surfactant |
|  | Neutral pH |
| CIP 150 | Anionic Surfactant |
|  | Sodium Hypochlorite |
|  | Silicates |
|  | Potassium Hydroxide |

In the healthcare industry, medical instruments and other articles may be cleaned manually, or by use of an automated washer apparatus (e.g., Amsco Reliance 444 washer from STERIS Corporation). In an automated washer apparatus a detergent, in liquid or powdered/granular form, is typically dispensed from a dispenser container (e.g., a detergent cup) as water is circulated therethrough to form a detergent solution. A peristaltic pump may be used to introduce a calibrated quantity of detergent solution into a washing chamber. However, there is no convenient or efficient manner to confirm that the detergent solution includes a proper detergent concentration. In this regard, a sample of the detergent solution is taken, and titration is performed to determine the detergent concentration therein. Since the detergent concentration is not determined continuously during a washing process, the automated washer apparatus will continue a washing process without alerting an operator of an improper detergent concentration. Typically, manual observation of detergent inside a detergent dispensing container is used to determine whether the detergent dispensing container needs to be replaced in order to provide a proper concentration of detergent in the detergent solution.

Titration of a detergent solution is time consuming, and is difficult and inconvenient to perform on a regular automated basis. Furthermore, the calibration of the peristaltic pump can change, as tubing becomes worn, the pump loses efficiency and/or the type of detergent is changed. The lack of a proper detergent concentration in the detergent solution can result in improperly cleaned medical instruments, increased reprocessing costs, and risks to patient safety. Furthermore, prior art processes for determining detergent concentration do not allow for fully automated procedures that can reduce human error.

In the pharmaceutical industry, two types of cleaning processes are commonly used to clean manufacturing equipment, namely, "clean in place" (CIP) and "clean out of place" (COP). A CIP process typically occurs by flowing or flooding equipment (e.g., process vessels, piping and ancillary equipment) with a detergent solution. CIP and COP processes can be automated or manual. However, a CIP process is usually an automated process, since it is typically used to clean large equipment that is difficult or awkward to clean manually. A COP process is ordinarily a manual cleaning process, since it is typically used to clean smaller or disassembled equipment. CIP and COP processes are both required to be "validated" processes. Accordingly, the CIP and COP processes must be well defined and tested, and must be conducted in a consistent manner each and every time. Accordingly, a measurement of the detergent concentration in the detergent solution must be made to verify that the proper detergent concentration is used. As discussed above, a sample of detergent solution can be taken and analyzed in a laboratory using standard techniques, such as titration. If the concentration of detergent in the detergent solution is determined to be improper, appropriate corrective action can be taken.

The foregoing analysis of detergent concentration is time consuming and is not done in real time. The time required for the off-line analyses can result in wasted resources and production delays. Furthermore, the process for determining detergent concentration does not allow for fully automated procedures that can reduce or eliminate human error.

The present invention provides a method and apparatus for monitoring the concentration of detergent used in a decontamination process, and addresses the aforementioned problems, as well as others.

SUMMARY OF THE INVENTION

In accordance with a first aspect of the present invention, there is provided a system for monitoring the concentration of a detergent in a detergent solution used for decontamination of an article, the system comprising: a capacitor having first and second electrical conductors exposed to the detergent solution, said detergent solution being a dielectric therebetween; and processing means for determining a measured value associated with an electrical property of the capacitor, said electrical property varying according to the concentration of the detergent in the detergent solution.

In accordance with another aspect of the present invention, there is provided a method for monitoring the concentration of a detergent in a detergent solution used for decontamination of an article, the method comprising: exposing a capacitor, having first and second electrical conductors, to the detergent solution, said detergent solution comprising a dielectric therebetween; and determining a measured value associated with an electrical property of the capacitor, said electrical property varying according to the concentration of the detergent in the detergent solution.

An advantage of the present invention is the provision of a method and apparatus for monitoring the concentration of a detergent in a detergent solution, wherein the detergent concentration is monitored in situ.

Another advantage of the present invention is the provision of a method and apparatus for monitoring the concentration of a detergent in a detergent solution that allows for data collection to verify detergent concentration.

Another advantage of the present invention is the provision of a method and apparatus for monitoring the concentration of a detergent in a detergent solution that reduces the time and complexity of monitoring detergent concentration.

Still another advantage of the present invention is the provision of a method and apparatus for monitoring the concentration of a detergent in a detergent solution that reduces the need to reprocess articles due to improper detergent concentration.

Still another advantage of the present invention is the provision of a method and apparatus for monitoring the concentration of a detergent in a detergent solution that can indicate to a user when a detergent concentration level is improper for a decontamination process.

Still another advantage of the present invention is the provision of a method and apparatus for monitoring the concentration of a detergent in a detergent solution that can reduce the amount of detergent introduced into the environment by controlling detergent concentration.

Yet another advantage of the present invention is the provision of a method and apparatus for monitoring the concentration of a detergent in a detergent solution that provides improved safety by limiting exposure to hazardous detergent solutions (e.g., highly acidic or alkaline detergent solutions).

These and other advantage will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
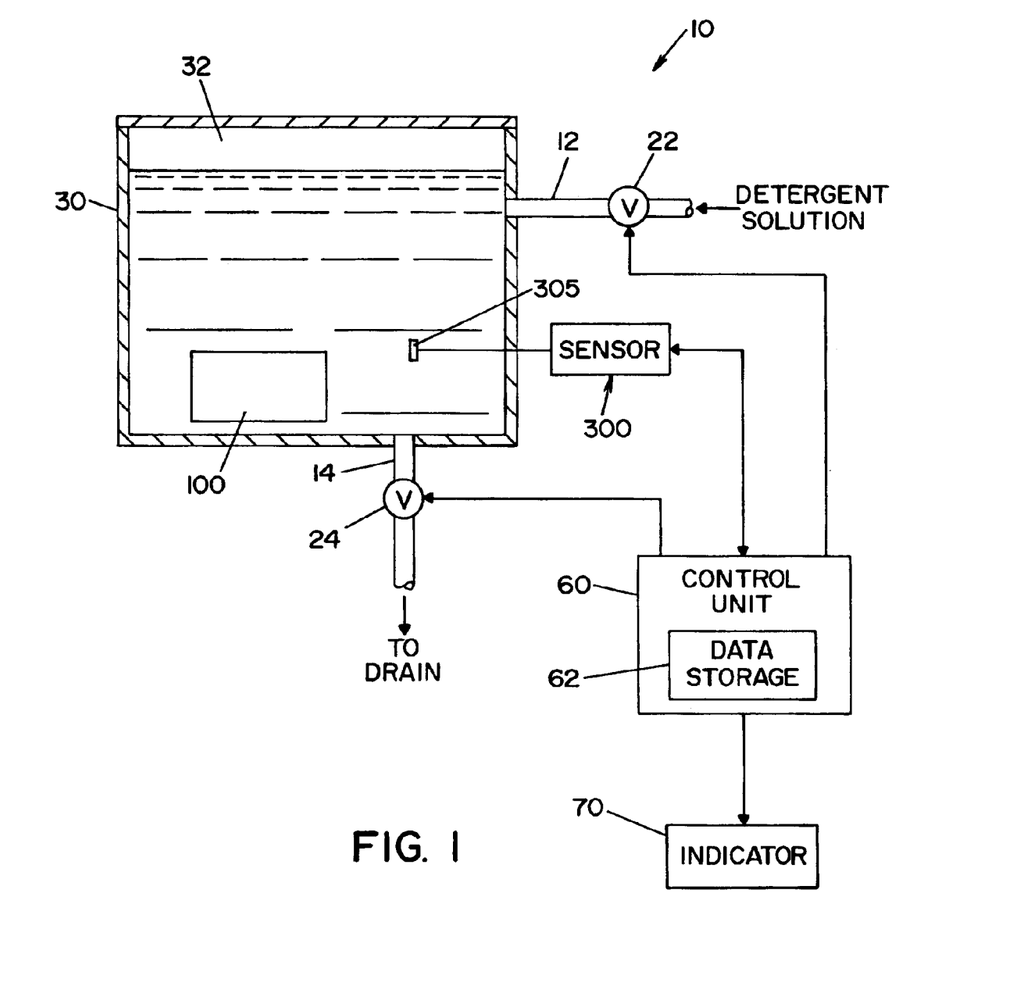
FIG. 1 is a simplified cross-sectional side view of a decontamination system for decontamination of articles used in healthcare (e.g., medical instruments and equipment) applications.

Referring now to the drawings wherein the showings are for the purpose of illustrating a preferred embodiment of the invention only, and not for the purpose of limiting same, FIG. 1 shows a decontamination system 10 having sensor 300 for monitoring the concentration of detergent within system 10. In the illustrated embodiment, decontamination system 10 is a washer for washing articles 100 (e.g., medical instruments and equipment). It should be understood that while an illustrated embodiment of the present invention is described with reference to a washer, it is contemplated that the present invention may be used in connection with other decontamination systems and facilities that utilize detergents.

System 10 is basically comprised of a vessel 30, a control unit 60, an indicator 70, and a sensor 300. Vessel 30 defines an enclosed chamber 32 dimensioned to receive one or more articles 100 to be washed. Articles 100 are placed inside chamber 32 for exposure to a detergent solution. In one embodiment, the detergent solution is comprised of detergent and water, wherein the detergent is comprised of one or more detergent chemical components, including, but not limited to, detergent chemical components identified in the table above.

Vessel 30 is fluidly connected with an input conduit 12 and an output conduit 14. A detergent solution (discussed below) flows into chamber 32 via input conduit 12. A valve 22 controls the flow of detergent solution into chamber 32. Output conduit 14 is in fluid communication with a drain. Valve 24 controls the flow of detergent solution through output conduit 14.

Control unit 60 is preferably a microprocessor or a microcontroller programmed to control operation of apparatus 10. In this regard, control unit 60 controls the operation of valves 22 and 24. Control unit 60 also preferably includes (or is connected with) a data storage device 62 for storing data.

Indicator 70 may take the form of a visual and/or an audible indicator, including, but not limited to, LEDs, LCDs, speaker, or alarm. In this regard, indicator 70 may be used to provide a visual and/or audible indication of the concentration of detergent in the detergent solution. In this regard, indicator 70 may change state in accordance with the detergent concentration. For instance, a green LED may be illuminated to indicate a proper detergent concentration, while a red LED may be illuminated to indicate an improper detergent concentration. Alternatively, an alarm can be sounded when the detergent concentration is determined to be improper.

Figure 2:
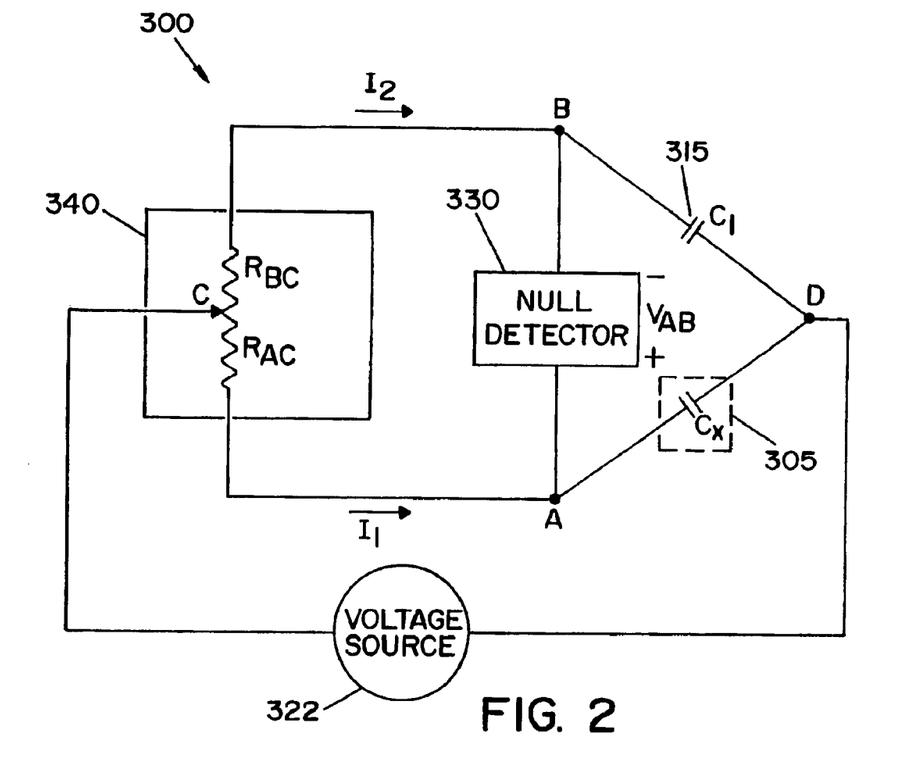
FIG. 2 is a schematic diagram of an exemplary capacitive sensor for monitoring the concentration of a detergent in a detergent solution, according to a first embodiment.

Sensor 300 may take the form of any suitable sensing device responsive to changes in detergent concentration. An exemplary sensor 300, is shown in FIG. 2. Sensor 300 is described in detail in U.S. patent application Ser. No. 10/389,036, filed Mar. 14, 2003, entitled "Method and Apparatus for Measuring Chemical Concentration in a Fluid," and U.S. patent application Ser. No. 10/405,880, filed Apr. 2, 2003, entitled "Method and Apparatus for Measuring Concentration of a Chemical Component in a Gas Mixture," which are fully incorporated herein in their entirety.

Sensor 300 is disposed within chamber 32 to sense the concentration of detergent in the detergent solution therein. However, it is contemplated that sensor 300 may alternatively be disposed at input conduit 12 and/or output conduit 14.

Sensor 300 includes a capacitor 305 that acts as a sensing element. Electrical properties of capacitor 305 are responsive to the concentration of the detergent in the detergent solution inside chamber 32. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

It should be appreciated that in an alternative embodiment, wherein sensor 300 is used in a process for cleaning pharmaceutical manufacturing equipment, sensing element 305 is located in a region where it will be exposed to the detergent solution, including, but not limited to, in-line with the pharmaceutical manufacturing equipment or the clean in place (CIP) pharmaceutical equipment.

According to the embodiment illustrated in FIG. 2, sensor 300 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. The bridge circuit is used to determine a capacitance value indicative of the detergent concentration inside chamber 32.

Sensor 300 is generally comprised of a voltage source 322, a null detector 330, an electronic potentiometer 340, a capacitor 315 of a known capacitance $C_1$, and capacitor 305 having a capacitance $C_x$.

Capacitor 305 is directly exposed to the detergent solution in chamber 32. The detergent solution fills the gap between the electrical conducting plates of capacitor 305, thereby acting as a "dielectric" of capacitor 305. Capacitance $C_x$ of capacitor 305 will vary in accordance with the concentration of the detergent in the detergent solution.

It should be appreciated that the conducting plates of capacitor 305 should be isolated from the detergent solution to prevent further damage to the conducting plates by the detergent. For example, a polymeric tube may be used to isolate the detergent solution from the plates, wherein the conducting plates are located outside the tube, and the detergent solution flows through the tube. Alternatively, a polymer coating may be applied to the conducting plates.

In one embodiment, capacitor 305 is a parallel plate capacitor. However, it should be appreciated that capacitor 305 could be constructed in a different form. For example, capacitor 305 could be a cylindrical or spherical capacitor. If a spherical capacitor is used as capacitor 305, holes must be placed in the outer shell of capacitor 305 such that the chemical solution can enter and exit the capacitor. The conducting plates may be made of copper. It should be understood that the term "plates" conventionally refers to the electrical conductors of a capacitor, irrespective of the geometry of the electrical conductors.

Electronic potentiometer 340 functions in the same manner as a mechanical potentiometer. In this regard, electronic potentiometer 340 is a three terminal device. Between two of the terminals is a resistive element. The third terminal known as the "wiper" is connected to various points along the resistive element. In the illustrated embodiment, the wiper is digitally controlled by control unit 60 (see FIG. 1). The wiper divides the resistive element into two resistors $R_{BC}$ and $R_{AC}$. Electronic potentiometer 340 may take the form of a digitally programmable potentiometer (DPPTM) available from Catalyst Semiconductor, Inc. of Sunnyvale, Calif.

In one embodiment, voltage source 322 provides an AC voltage signal, such as a sinusoidal or pulse waveform. Null detector 330 is a device for detecting a null condition (i.e., a short circuit), such as a galvanometer, a voltmeter, a frequency-selective amplifier, and the like.

Operation of sensor 300 will now be described in detail. The elements of the bridge circuit are connected between junctions AC, BC, AD, and BD. Electronic potentiometer 340 is operated by control unit 60 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC} = V_{BC}, \text{ and } V_{AD} = V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC} = V_{BD}/V_{BC}$$

$$V_{AD} = V_{BD}/(V_{AC}/V_{BC})$$

Capacitor 305 of capacitance $C_x$ is connected between junctions A and D, and capacitor 315 of known capacitance $C_1$ is connected between junctions B and D. Electronic potentiometer 340, connected from junction A to junction C to junction B, is adjusted by control unit 60 to vary the voltages $V_{AC}$ and $V_{BC}$.

When a null is detected by null detector 330, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC} = I_1 R_{AC} \text{ and } V_{BC} = I_2 R_{BC}.$$

The voltage across a capacitor with capacitance C, current I, and frequency is:

$$V = \frac{I}{2\pi f C}$$

Therefore, the voltages $V_{AD}$ and $V_{BD}$ may be expressed as:

$$V_{AD} = \frac{I_1}{2\pi f C_x} \quad V_{BD} = \frac{I_2}{2\pi f C_1}$$

As discussed above, $V_{AD} = V_{BD}/(V_{AC}/V_{BC})$, $V_{AC} = I_1 R_{AC}$, and $V_{BC} = I_2 R_{BC}$. Therefore, $$C_x = C_1 \left( \frac{R_{BC}}{R_{AC}} \right).$$

In view of the forgoing relationship, when a null condition is detected, the resistance values for $R_{BC}$ and $R_{AC}$, along with the known capacitance $C_1$ of capacitor 315, can be used to determine the unknown value of capacitance $C_x$ of capacitor 305.

Differences in dipole moments of different molecules between the plates of capacitor 305 will affect the electrical properties (e.g., dielectric constant) of capacitor 305. Similarly, the presence of free charges between the plates of capacitor 305 will affect the electrical properties of capacitor 305. Changes to the electrical properties of capacitor 305 are used to monitor the detergent concentration in the detergent solution. As discussed above, detergent solution fills the gap between the conducting plates of capacitor 305, thereby acting as the dielectric of capacitor 305. By configuring capacitor 305 as an element of a bridge circuit, a measure of resistance values $R_{AC}$ and $R_{BC}$, when the bridge is balanced or nulled, can be used to determine the capacitance $C_x$ of capacitor 305. The capacitance $C_x$ of capacitor 305 is indicative of the concentration of the detergent in the detergent solution, since the permittivity of the respective dielectric is affected by the detergent concentration.

It is well known that for a parallel plate capacitor $C = (k \epsilon_0)(A/d) = (\epsilon)(A/d)$, where C is capacitance, k is the dielectric constant, $\epsilon_0$ is the permittivity of free space ($8.85 \times 10^{-12}$ F/m), $\epsilon$ is the permittivity (Farads/meter) of the capacitor dielectric, A is the area of the capacitor plates (m$^2$), and d is the separation in meters between the capacitor plates. As $\epsilon$ increases, the capacitance C will increase. Where the capacitor is a parallel plate capacitor with circular plates of diameter D, $C = (\pi D^2)/(4d)$.

It will be appreciated that the dielectric constant k of the capacitor can be determined according to the following expression:

$$k = \frac{4dC}{\pi D^2 \epsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c = 1/(2\pi f C)$). Accordingly, frequency of the waveform generated by voltage source 322 influences the response of capacitors. Thus, the frequency selected for voltage source 322 should preferably be a frequency that will provide a generally linear response for capacitance as the concentration of detergent component in the detergent solution is varied. This will facilitate the use of interpolation and extrapolation of capacitance values, as will be discussed further below. If a suitable linear response is not obtained, then an expanded set of data points should be stored in data storage device 62.

Figure 3:
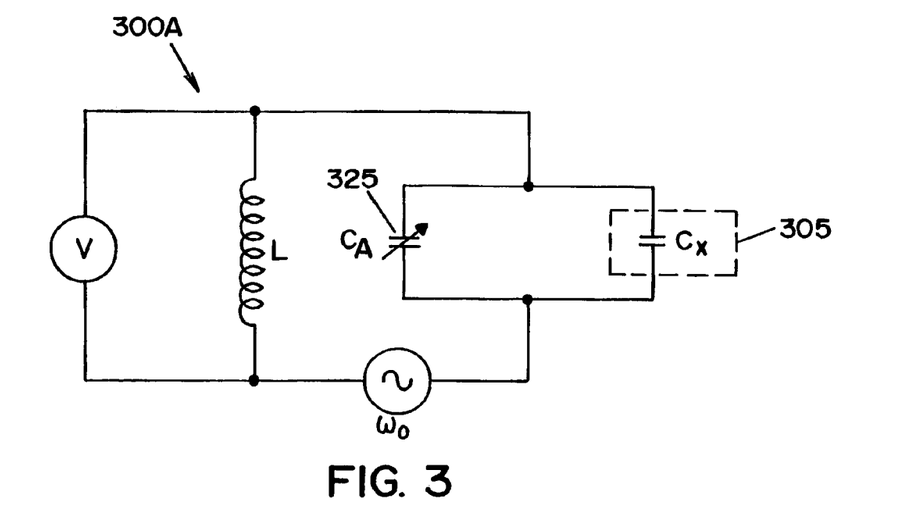
FIG. 3 is a schematic diagram of an exemplary capacitive sensor for monitoring the concentration of a detergent in a detergent solution, according to a second embodiment.

It should be appreciated that while in one embodiment of the present invention includes a sensor 300 in the form of a bridge circuit, other types of circuits and techniques (including other types of bridge circuits, and capacitance meters) known to those skilled in the art, may be suitably used to measure capacitance. For example, FIG. 3 illustrates an alternative sensor 300A. Sensor 300A is an LC resonant circuit, including a variable capacitor 325 (having a capacitance $C_A$), and capacitor 305 (having a capacitance $C_x$) that acts as the sensing element, as described above. Since the resonance frequency $\omega_0 = [L(C_A + C_x)]^{-1/2}$, the unknown capacitance $C_x$ of capacitor 305 can be determined.

Figure 4:
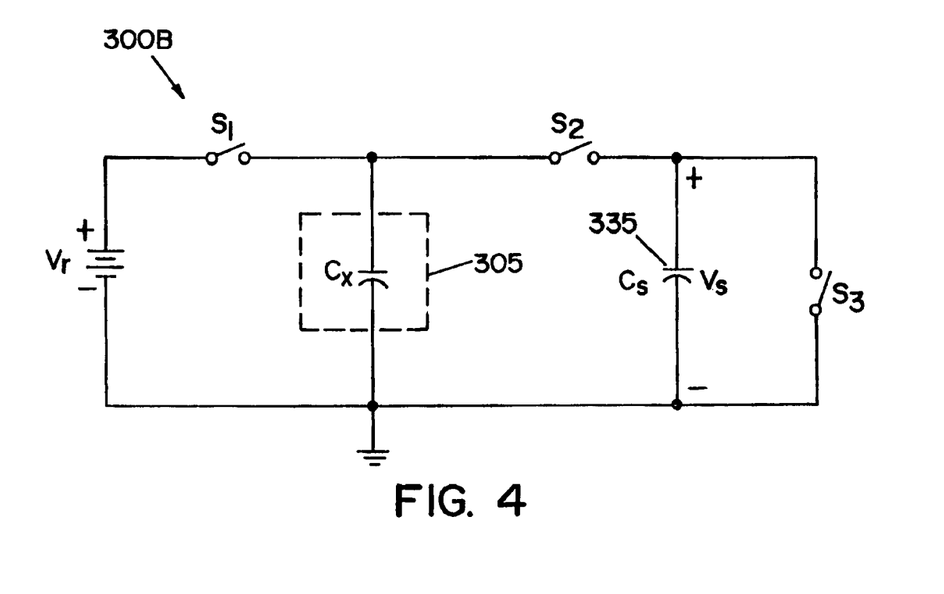
FIG. 4 is a schematic diagram of an exemplary capacitive sensor for monitoring the concentration of a detergent in a detergent solution, according to a third embodiment.

FIG. 4 illustrates yet another alternative sensor 300B suitable for use in connection with the present invention. Sensor 300B is a "charge transfer" sensor circuit. Charge transfer sensor circuits are recognized to provide resolutions of fractions of a femtoFarad. In a charge transfer sensor circuit the unknown capacitance $C_x$ of a sense electrode is determined by charging the sense electrode to a fixed potential, and then transferring that charge to a charge detector comprising a capacitor 335 of known capacitance $C_s$. In sensor 300B, capacitor 305 of unknown capacitance $C_x$ acts as a sensing element, as described above. In this regard, detergent solution in chamber 32 fills the gap between the conducting plates of capacitor 305, thereby acting as "dielectric" of capacitor 305. Capacitor 305 is first connected to a DC reference voltage ($V_r$) via a switch $S_1$. Switch $S_1$ is reopened after capacitor 305 is satisfactorily charged to the potential of $V_r$. Then, after as brief as possible a delay so as to minimize leakage effects caused by conductance, switch $S_2$ is closed and the charge (Q) present on capacitor 305 is transferred to capacitor 335 (i.e., the charge detector). Once the charge Q is satisfactorily transferred to capacitor 335, switch $S_2$ is reopened. By reading voltage $V_s$, the capacitance $C_x$ of capacitor 305 can be determined. $V_s$ may be input to an amplifier to provide the scaling necessary to present an analog-to-digital converter (ADC) with a useful range of voltage for digital processing. Switch $S_3$ acts as a reset means to reset the charge between charge transfer cycles, so that each charge transfer cycle has a consistent initial condition. Switches $S_1$, $S_2$ and $S_3$ may be electromechanical switches or transistors. Preferably, digital control logic is used to control switches $S_1$, $S_2$ and $S_3$. In one embodiment, capacitor 335 is selected to be significantly larger than capacitor 305.

The equations governing sensor 300B are as follows:

$V_s=V_r[C_y/(C_y+C_s)]$, therefore $C_y=V_sC_s/[V_r-V_s]$.

The charge-transfer sensor has been applied in a self-contained capacitance-to-digital-converter (CDC) integrated circuit (IC). For example, Quantum Research Group produces a QProx™ CDC sensor IC (e.g., QT300 and QT301 CDC sensor ICs) for detecting femtofarad level changes in capacitance. The CDC sensor IC outputs a digital value corresponding to the detected input capacitance. The value of an external sampling capacitor controls the gain of the sensor. Quantum Research Group also produces a QTM2000 module for capacitance-based sensing. The QTM2000 uses the QT9701B2 charge-transfer capacitance sensor IC, and operates in conjunction with an E297S board. The QT9701B2 can sense capacitance in the range of sub-femtofarads.

Other high sensitivity circuitry is provided by such devices as the PTL 110 capacitance transducer from Process Tomography Limited of Cheshire, United Kingdom. The PTL 110 measures small values of capacitance (up to 10 picoFarads) with a resolution of 1 femtoFarad. A 1616 Precision Capacitance Bridge from IET Labs, Inc. of Westbury, N.Y., allows for measurement of capacitances in the range from $10^{-7}$ pF to 10 $\mu$F. Tektronix produces the Tektronix 130 LC Meter that measures capacitance from 0.3 pF to 3 pF. It has also been acknowledged in the prior art literature that capacitance sensor circuits using modern operational amplifiers and analog-to-digital converters (ADCs) can easily obtain resolutions to 0.01 pF.

Referring now to FIG. 2, monitoring of detergent concentration in the detergent solution inside chamber 32 will now be described in connection with sensor 300.

Capacitor 305 is nulled in water used for diluting the detergent. Thereafter, capacitor 305 is exposed to known concentrations of a detergent in a detergent solution to develop a set of data, or a curve, of capacitance values $C_x$ as a function of concentration of detergent in the detergent solution. The associated set of data, or curve, is programmed or stored in data storage device 62 of control unit 60. As the concentration of the detergent is varied in the detergent solution, the corresponding capacitance $C_x$ of capacitor 305 is determined, and stored in data storage device 62.

It should be understood that introduction of a detergent may increase or decrease the dielectric constant of the water, depending on the composition of the detergent. In this respect, a highly ionic detergent will increase the dielectric constant of water, while a highly non-polar organic detergent will decrease the dielectric constant of water.

After the set of data is stored in data storage device 62 for the detergent solution, monitoring of the concentration of detergent in the detergent solution can commence. Capacitor 305 is exposed to a detergent solution in chamber 32, and a value for the capacitance $C_x$ of capacitor 305 is determined. The data stored in data storage device 62 is then searched for the measured capacitance value $C_x$ to obtain the corresponding detergent concentration.

A linear relationship between detergent concentration and capacitance allows one to normalize any measurement made so as to provide the absolute concentration of the detergent. If the measured capacitance $C_x$ of capacitor 305 is not found in the pre-stored data, the stored data may be interpolated or extrapolated to obtain a detergent concentration corresponding to the measure capacitance $C_x$ of capacitor 305. As noted above, frequency of the waveform generated by voltage source 322 will influence the response of capacitors. Where the capacitance $C_x$ of capacitor 305 does not exhibit a suitable linear response, an expanded set of data points should be stored in data storage device 62, so that interpolation or extrapolation is unnecessary.

It should be appreciated that while a preferred embodiment of the present invention uses a measure of a capacitor's capacitance to monitor detergent concentration, it is also contemplated that a measure of other electrical properties associated with a capacitor may be used to monitor detergent concentration, including, but not limited to, the permittivity and dielectric constant of the capacitor dielectric.

The present invention shall now be further described with reference to the operation of system 10 (FIG. 1). An article 100 is placed inside chamber 32 of vessel 30. Control unit 60 controls valve 22 to allow a detergent solution to enter chamber 32. Detergent solution is removed from chamber 32 via outlet conduit 16. Article 100 is exposed to the detergent solution circulating inside chamber 32.

Sensor 300 monitors the detergent concentration in the detergent solution inside chamber 32. In this regard, capacitor 305 is exposed to the detergent solution in chamber 32 during a washing process. The measured capacitance $C_x$ of capacitor 305 is compared to the pre-stored values of capacitance $C_x$ to obtain the corresponding detergent concentration.

In response to detecting a detergent concentration that is improper, corrective action can be taken by control unit 60, including, but not limited to, increasing or decreasing the amount of detergent or water in the detergent solution, or reprocessing the articles in chamber 32.

It should be appreciated that in alternative embodiment of the present invention, a capacitance $C_x$ of capacitor 305 can be established as a setpoint value (e.g., a minimum detergent concentration). As a preliminary step, capacitor 305 is first nulled in 100% water, and a value is obtained for capacitance $C_x$ of capacitor 305 in the presence of a detergent solution having a minimum detergent concentration for proper decontamination. This value for capacitance $C_x$ is then preferably stored in data storage device 62 as a setpoint value. It should be appreciated that alternative values can be used for the setpoint value. Sensor 300 can now be used to monitor the detergent concentration in the detergent solution inside chamber 32. The measured capacitance $C_x$ of capacitor 305 is compared to the setpoint value. If the measured capacitance $C_x$ differs a predetermined amount from the setpoint value, then it is determined that the detergent concentration is improper for decontamination. In this case, control unit 60 may provide an audible and/or visual indicator to the operator.

It should be understood that data collected by sensor 300 during a decontamination process may also be stored in data storage device 62 to provide historical data for verification of appropriate processing conditions.

In accordance with an alternative embodiment of the present invention, system 10 further includes an electronic weighing device (not shown). By way of example, and not limitation, the electronic weighing device may take the form of a conventional load cell, or other force transducer device. The electronic weighing device is located inside chamber 32 to provide a signal to control unit 60 indicative of the weight of a load of articles located in chamber 32. Control unit 60 is programmed to determine a detergent concentration for the detergent solution that is appropriate for proper decontamination of the load of articles. In this regard, system 10 will produce a chemical solution, in accordance with the determined detergent concentration, by combining an appropriate amount of detergent (e.g., in powdered or liquid form) with water. Appropriate adjustments can be made to the detergent concentration during a decontamination process in accordance with the sensed detergent concentration. Furthermore, after a decontamination process has been completed, sensor 300 can be used to determine whether all of the detergent has been removed from chamber 32 during a rinse cycle.

Figure 5:
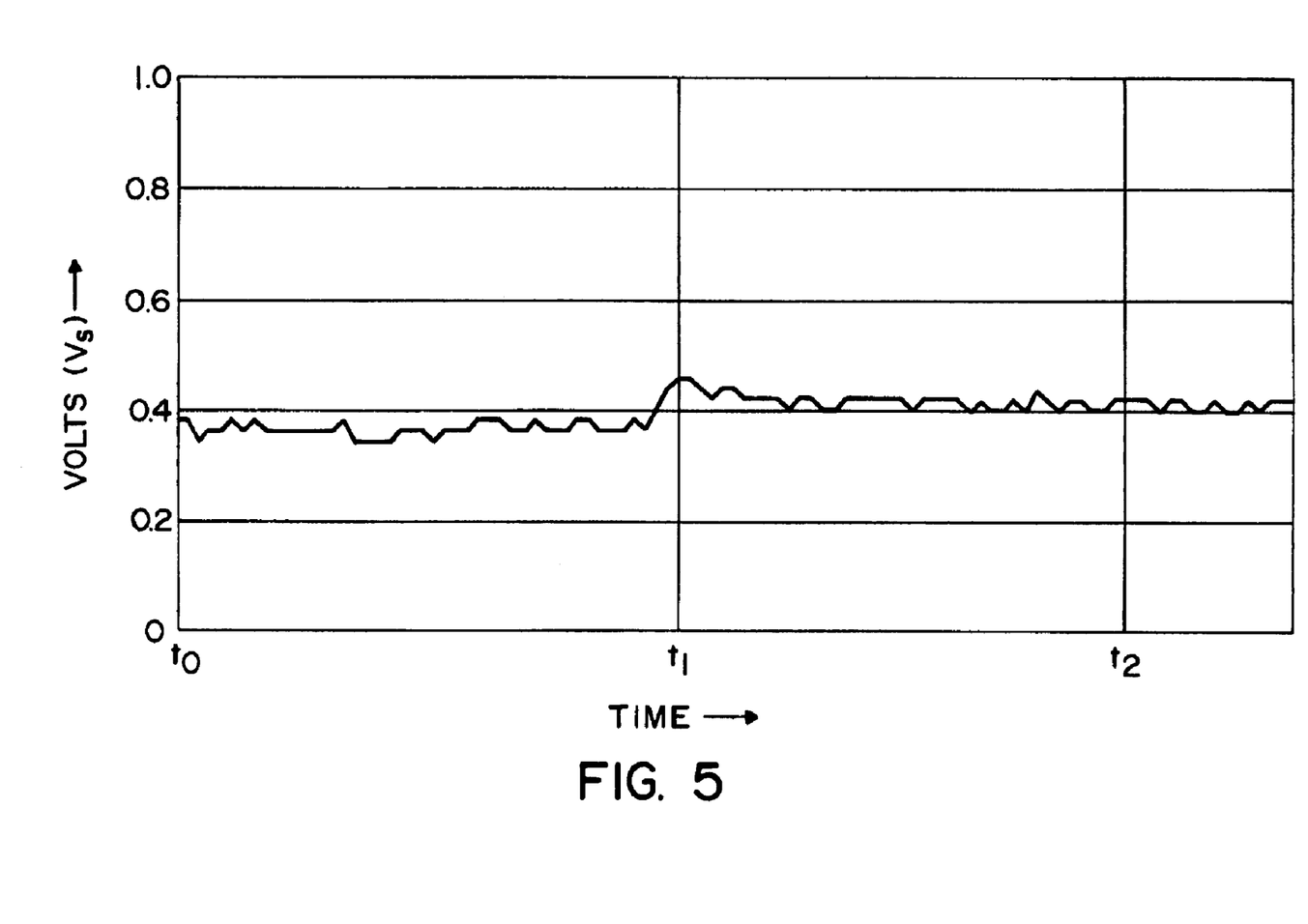
FIG. 5 is a graph showing the response of a capacitive sensor to the introduction of 1 ml of Renu-Klenz detergent to 10 L of water, as a function of time.
Figure 6:
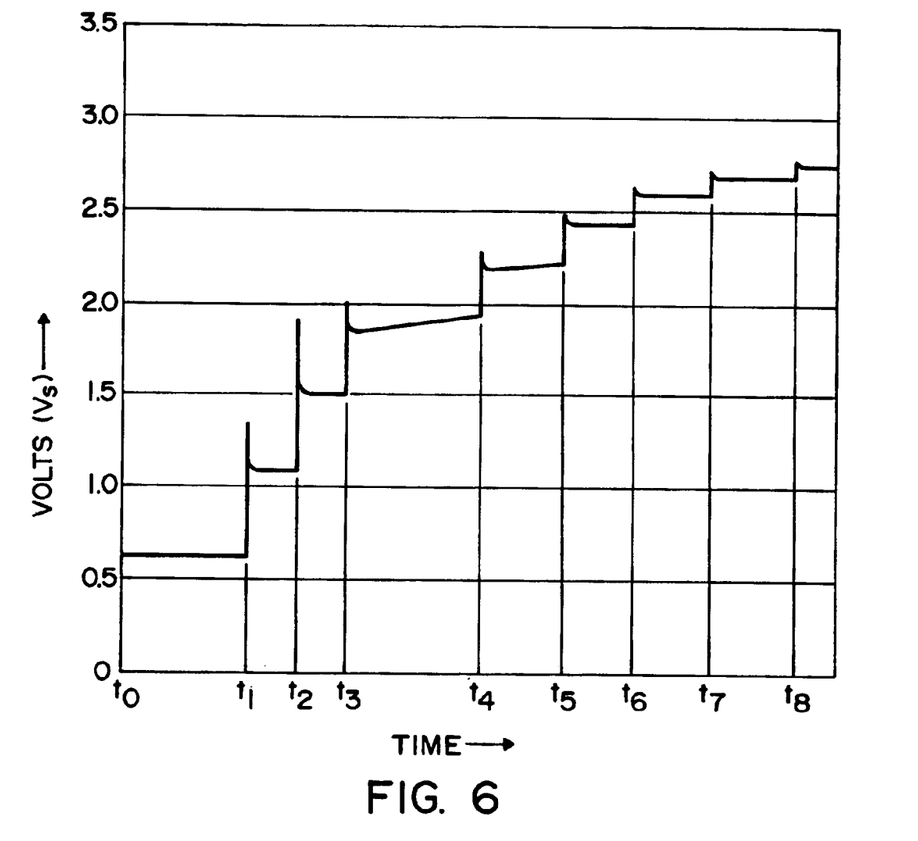
FIG. 6 is a graph showing the response of a capacitive sensor to the introduction of 10 ml increments of Liqui-Jet 2 detergent to 10 L of water, as a function of time.

Test data, shown in FIGS. 5 and 6, was collected using a charge transfer sensor (i.e., Quantum Research Group QProX™ E297 Evaluation Board employing the QProx™ QT9701B2 Charge Transfer Capacitance Sensor IC) to detect changes in detergent concentration of a detergent solution passing through an enclosed tubular path. Basic operation of a charge-transfer sensor circuit is described above in connection with FIG. 4. A charge transfer sensor is based on the conservation of charge, using the fact that when a capacitor holding a charge is connected to an uncharged capacitor, the first capacitor will transfer a portion of its charge to the second without a net loss of charge.

With reference to the circuit shown in FIG. 4, a sheet of copper foil serves as an external sense electrode, having an unknown capacitance of $C_x$ to earth (capacitor 305). The sense electrode is connected to a second capacitor (on a Qprox™ E297S board) having a known capacitance $C_s$ (capacitor 335). To commence a charge transfer cycle, switch $S_3$ is held closed briefly to ensure that capacitor 335 of capacitance $C_s$ is discharged. Capacitor 305, having capacitance $C_x$, is first charged to a reference voltage $V_r$ via the closing of switch $S_1$. $S_1$ is reopened after capacitor 305 has satisfactorily charged up to a reference voltage $V_r$. Thereafter, switch $S_2$ is briefly closed to transfer the charge from capacitor 305 to capacitor 335. The resulting voltage $V_s$ of capacitor 335 is amplified, converted to digital, and further processed. Voltage $V_s$ is indicative of capacitance $C_x$. The charge transfer cycle continuously repeats, executed via bursts of pulses on lines controlling the switches. The switches are MOSFET-type transistors.

Referring now to FIG. 5, there is shown a graph illustrating the response of a capacitive sensor to the introduction of 1 ml of Renu-Klenz detergent to 10 L of water, as a function of time. For the illustrated data, a tank was filled with 10 L of water, and at time $t_I$, 1 ml of Renu-Klenz was added directly into the tank. A charge transfer capacitance sensor IC (Qprox QT9701B2) was used to sense the presence detergent. As can be observed from FIG. 5, the voltage of the capacitance sensor changes from the original voltage (associated with only 10 L of water in the tank) to a new voltage, after the 1 ml of detergent has been added to the 10 L of water. A short spike in the voltage is observed as the detergent is being added to the water.

FIG. 6 is a graph showing the response of a capacitive sensor to the introduction of 10 ml increments of Liqui-Jet 2 detergent to 10L of water, as a function of time. A charge transfer capacitance sensor IC (Qprox QT9701B2) was used to sense the presence detergent. At time $t_0$, 10 L of water is circulated in a tank at 55° C. An additional 10 mL of detergent is added at times $t_1$, $t_2$, $t_3$, $t_4$, $t_5$, $t_6$, $t_7$, and $t_8$. Accordingly, a range of 10 mL to 80 mL of detergent is shown. Each additional increment of 10 mL of detergent is added only after equilibrium is established.

It is further contemplated that the present invention can also be used to distinguish between the presence of different detergents inside chamber 32. In this regard, capacitive sensor 300 will respond differently to detergents having different detergent chemical components. In this manner, control unit 60 may be programmed to ascertain whether the detergent present inside chamber 32 meets a predetermined criteria, including, but not limited to, suitability for a desired decontamination process, and/or whether the detergent has been approved for use with the decontamination system by the manufacturer of the decontamination system. For instance, if control unit 60 detects the presence of an unsuitable and/or unapproved detergent based upon the sensed capacitance (or other electrical property of the capacitor), control unit 60 can be programmed to take one or more actions, including, but not limited to, alerting the operator to the detected condition using indicator 70, and/or preventing decontamination system 10 from commencing or continuing a decontamination process.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A system for monitoring the concentration of a detergent in a detergent solution used for decontamination of an article, the system comprising:

sensing means responsive to changes in the concentration of the detergent in the detergent solution to produce an output signal indicative of a measured detergent concentration, said sensing means including a capacitor having first and second electrical conductors exposed to the detergent solution, wherein said detergent solution comprises a dielectric therebetween, said capacitor having an electrical property that varies according to the concentration of the detergent in the detergent solution;

a memory for storing a set of data including (a) measured values associated with the electrical property of the capacitor and (b) corresponding detergent concentration values indicative of the concentration of the detergent in the detergent solution;

processing means for receiving the output signal from the sensing means and determining the concentration of the detergent in the detergent solution by accessing the set of data stored in the memory.

2. A system according to claim 1, wherein said memory stores a setpoint value associated with said electrical property.

3. A system according to claim 2, wherein said processing means includes means for determining whether the concentration of the detergent exceeds the setpoint value by a predetermined amount.

4. A system according to claim 1, wherein said system further comprises:

a bridge circuit, wherein said capacitor forms a part of the bridge circuit.

5. A system according to claim 1, wherein said system further comprises:
a charge transfer circuit, wherein said capacitor forms a part of the charge transfer sensor circuit.

6. A system according to claim 1, wherein said detergent is selected from the group consisting of: enzymatic, alkaline, acidic, oxidative, neutral, inorganic-based and organic-based detergent chemical components.

7. A system according to claim 1, wherein said system further comprises an electronic weighing device for determining the weight of the one or more articles being decontaminated, said weight being used to determine an appropriate concentration of the detergent in the detergent solution.

8. A method for monitoring the concentration of a detergent in a detergent solution used for decontamination of an article, the method comprising:
exposing a capacitor, having first and second electrical conductors, to the detergent solution, said detergent solution comprising a dielectric therebetween, said capacitor having an electrical property that varies according to the concentration of the detergent in the detergent solution, and producing an output signal indicative of a measured detergent concentration; and
pre-storing data including (a) measured values associated with the electrical property and (b) corresponding concentration values indicative of the concentration of the detergent in the detergent solution;
determining the concentration of the detergent in the detergent solution by using the output signal and accessing the pre-stored data.

9. A method according to claim 8, wherein the method further comprises:
determining whether the concentration of the detergent solution exceeds a setpoint value by a predetermined amount.

10. A method according to claim 8, wherein said capacitor forms a part of a bridge circuit.

11. A method according to claim 8, wherein said capacitor forms a part of a charge transfer sensor circuit.

12. A method according to claim 8, wherein said detergent is selected from the group consisting of: enzymatic, alkaline, acidic, oxidative, neutral, inorganic-based and organic-based detergent chemical components.

13. A method according to claim 8, wherein said method further comprises the step of:
determining the weight of one or more articles being decontaminated, using an electronic weighing device, said weight being used to determine an appropriate concentration of the detergent in the detergent solution.

14. A system for detecting a detergent for decontamination of an article in a decontamination system, the system comprising:
sensing means responsive to chemical components of a detergent to produce an output signal indicative of the detergent, said sensing means including a capacitor having first and second electrical conductors exposed to the detergent, wherein said detergent comprises a dielectric therebetween, said capacitor having an electrical property that varies according to the chemical components of the detergent; and
processing means for determining whether the detergent meets a predetermined criterion based upon the output signal produced by the sensing means, said processing means preventing the decontamination system from decontaminating the article in the event that the predetermined criterion has been met, said predetermined criterion being one of: (a) the detergent is not a suitable detergent for decontamination of the article, or (b) the detergent is not an approved detergent for use with the decontamination system.

15. A system according to claim 14, wherein said processing means activates an indicator when said predetermined criterion has been met.

16. A method for detecting a detergent for decontamination of an article in a decontamination system, the method comprising:
exposing a capacitor, having first and second electrical conductors, to the detergent, said detergent comprising a dielectric therebetween, said capacitor having an electrical property that varies according to the chemical components of the detergent;
producing an output signal indicative of chemical components of the detergent;
determining whether the detergent meets a predetermined criterion based upon the output signal; and
preventing the decontamination system from decontaminating the article in the event that the predetermined criterion has been met, said predetermined criterion being one of: (a) the detergent is not suitable for decontamination of the article, or (b) the detergent has not been approved for use with the decontamination system.

17. A method according to claim 16, wherein an indicator is activated when the predetermined criterion has been met.

* * * * *